(12) United States Patent
Dori et al.

(10) Patent No.: US 12,337,107 B2
(45) Date of Patent: Jun. 24, 2025

(54) PERSONAL EXHALED AIR REMOVAL SYSTEM AND METHOD

(71) Applicants: Guy Dori, Haifa (IL); Shay Brikman, Ramat Zvi (IL); Ofer Pintel, Matan (IL)

(72) Inventors: Guy Dori, Haifa (IL); Shay Brikman, Ramat Zvi (IL)

(*) Notice: Subject to any disclaimer, the term of this patent is extended or adjusted under 35 U.S.C. 154(b) by 0 days.

(21) Appl. No.: 18/008,973

(22) PCT Filed: Jun. 9, 2021

(86) PCT No.: PCT/IL2021/050695
§ 371 (c)(1),
(2) Date: Dec. 8, 2022

(87) PCT Pub. No.: WO2021/250670
PCT Pub. Date: Dec. 16, 2021

(65) Prior Publication Data
US 2023/0218841 A1    Jul. 13, 2023

(30) Foreign Application Priority Data
Jun. 11, 2020 (IL) .......................... 275299

(51) Int. Cl.
| | |
|---|---|
| *A61M 16/00* | (2006.01) |
| *A41D 13/11* | (2006.01) |
| *A61M 16/06* | (2006.01) |
| *A61M 16/10* | (2006.01) |
| *A61M 16/14* | (2006.01) |

(52) U.S. Cl.
CPC ..... *A61M 16/0009* (2014.02); *A41D 13/1184* (2013.01); *A61M 16/0096* (2013.01); *A61M 16/0666* (2013.01); *A61M 16/1005* (2014.02); *A61M 16/14* (2013.01); *A61M 2205/3368* (2013.01); *A61M 2230/42* (2013.01)

(58) Field of Classification Search
CPC ...... A41D 13/11; A41D 13/1184; A61B 1/00; A61B 5/00; A61B 5/0816; A61B 5/097; A61G 10/005; A61M 1/00; A61M 16/0009; A61M 16/0096; A61M 16/0666; A61M 16/1005; A61M 16/14; A61M 2205/3368; A61M 2230/42
See application file for complete search history.

(56) References Cited

U.S. PATENT DOCUMENTS

| | | | | |
|---|---|---|---|---|
| 3,747,599 | A | * | 7/1973 | Malmin ................. A41D 13/11 128/201.12 |
| 4,312,339 | A | | 1/1982 | Thompson |

(Continued)

FOREIGN PATENT DOCUMENTS

| | | |
|---|---|---|
| WO | 2007/047286 | 4/2007 |

*Primary Examiner* — Colin W Stuart
*Assistant Examiner* — Douglas Y Sul
(74) *Attorney, Agent, or Firm* — The Law Office of Joseph L. Felber

(57) ABSTRACT

A personal exhaled air removal (PEAR) system for removing/evacuating exhaled air from a vicinity of a patient is designed to remove the exhaled air during an exhalation cycle of a patient. The system is synchronized with a patient's breathing cycle for activating suction of exhaled air via at least one suction inlet, and the suction inlet is adjacent to the patient, possibly attached to the patient via an interface.

18 Claims, 10 Drawing Sheets

(56) References Cited

U.S. PATENT DOCUMENTS

| | | | |
|---|---|---|---|
| 4,608,976 A | 9/1986 | Suchy | |
| 4,895,172 A * | 1/1990 | Lindkvist | A61M 16/009 |
| | | | 128/863 |
| 5,676,133 A | 10/1997 | Hickle et al. | |
| 5,715,813 A * | 2/1998 | Guevrekian | A61M 16/009 |
| | | | 128/205.12 |
| 6,076,524 A | 6/2000 | Corn | |
| 6,237,596 B1 * | 5/2001 | Bohmfalk | A41D 13/1123 |
| | | | 128/911 |
| 6,247,470 B1 | 6/2001 | Ketchedjian | |
| 7,152,604 B2 | 12/2006 | Hickle et al. | |
| 7,513,252 B2 * | 4/2009 | Berg | A61M 16/009 |
| | | | 128/205.12 |
| 8,925,548 B2 | 1/2015 | Pierro et al. | |
| 9,055,888 B2 | 6/2015 | Levitsky et al. | |
| 9,364,633 B2 | 6/2016 | Mayo | |
| 10,393,399 B2 | 8/2019 | Hilbig et al. | |
| 2004/0055596 A1 * | 3/2004 | Bacon | A61M 15/0093 |
| | | | 128/200.11 |
| 2009/0235932 A1 * | 9/2009 | Nashed | A61M 16/0816 |
| | | | 128/203.29 |
| 2010/0234794 A1 | 9/2010 | Weadock et al. | |
| 2016/0310769 A1 | 10/2016 | Tang et al. | |
| 2017/0165448 A1 * | 6/2017 | Nibhanipudi | A61M 16/16 |
| 2017/0304575 A1 | 10/2017 | Boulanger | |
| 2018/0071469 A1 | 3/2018 | Oldfield et al. | |
| 2018/0311515 A1 | 11/2018 | Wilson et al. | |

\* cited by examiner

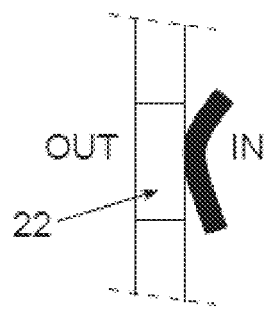
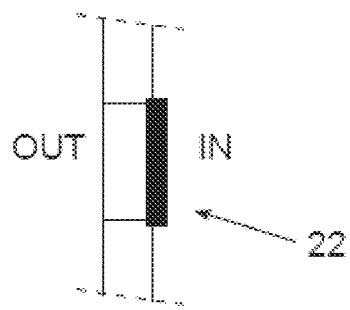
Fig. 9B    Fig. 9C
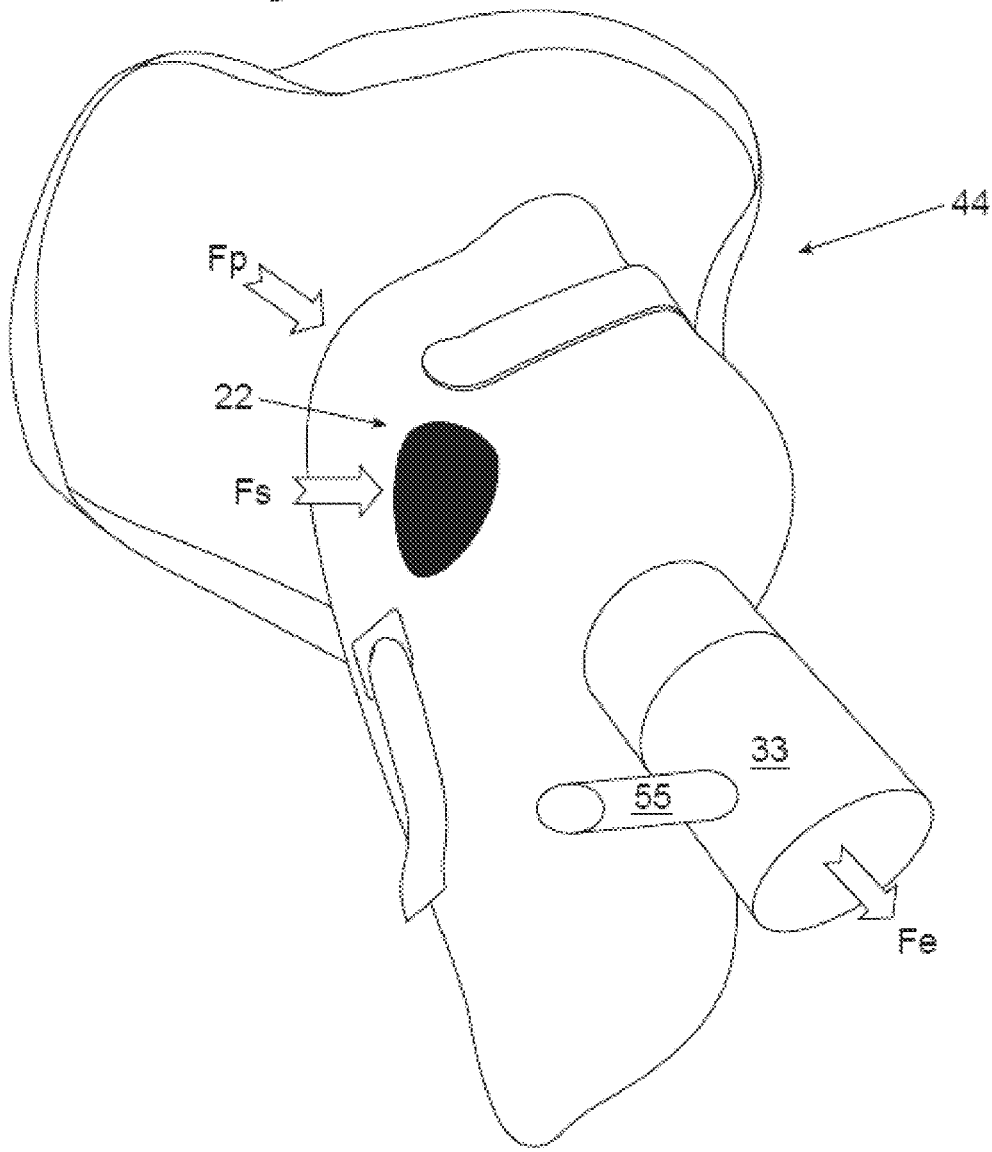
Fig. 9A

PERSONAL EXHALED AIR REMOVAL SYSTEM AND METHOD

TECHNICAL FIELD

Embodiments of the invention relate to a personal exhaled air removal (PEAR) system and method, preferably for removing potential contaminated exhaled air of a patient from the patient's vicinity and/or from mixing with air within a room where he/she is placed.

BACKGROUND

Air within a facility (e.g. old age home, hospital, examination rooms for bronchoscopy or gastroscopy, dentist office, or the like, ambulance) may be exposed to contamination due to e.g. secretions exhaled by dwellers of the facility. This may be increasingly problematic, for example, when infectious disease (such as those caused by viruses, e.g. the novel corona virus SARS-Cov2 or COVID-19) spread across large regions affecting substantial numbers of people.

Contaminated material from a patient's exhaled breath may be secreted by the actions of breathing, coughing, sneezing or talking. Contaminated and contagious secreted material (viruses or bacteria for example) may spread in room air or float in air or land on surfaces of objects in the room or on humans.

Such contaminated material remains viable for various periods of time and if individuals are in contact with this material they may ingest or inhale it and become infected and ill [van Doremalen et al. N Engl. J Med 2020; 382: 15644567; COVID-19 and Workers Compensation: Modeling Potential Impacts. Executive summary to NCCI (National Council on Compensation insurance) white paper April 2020]. Therefore, when room air is aerosolized with contaminating materials, it may instantly become a source for transmitting disease to other individuals.

Examples of pathogens that may possibly contaminate room air from a patient's exhaled air may include: Bordetella pertussis, influenza virus, adenovirus, rhinovirus, Mycoplasma pneumoniae, SARS-associated coronavirus (SARS-CoV), group A streptococcus, and Neisseria meningitides, and currently the novel corona virus (SARS-Cov-2), all by droplet aerosols.

Examples of pathogens that may possibly contaminate air by airborne droplet nuclei may include: Mycobacterium tuberculosis, rubeola virus (measles), and varicella-zoster virus (chickenpox) [Siegel J D et al. 2007 Guideline for Isolation Precautions: Preventing Transmission of infectious Agents in Healthcare Settings.

Contamination of air due to a patient's contagious exhaled air can be enhanced by supportive measures aiding a patient to breathe, such as respiratory devices providing gases (e.g. oxygen) to such patients. Examples of such respiratory devices may include: high-flow oxygen (HFO) devices (for example high flow therapy nasal cannula system of Vapotherm Inc.), devices suitable for providing medications via nebulizers (or the like). Observations suggest that HFO devices increase the spread of exhaled material in a room, and likewise nebulizers increase the spread of aerosolized material further in room air.

The following article addresses the aforementioned: [James A. McGrath, Andrew O'Sullivan, Gavin Bennett, Ciarrai O'Toole, Mary Joyce, Miriam A. Byrne, and Ronan MacLoughlin Investigation of the Quantity of Exhaled Aerosols Released into the Environment during Nebulisation. Pharmaceutics. 2019 February; 11(2): 75].

As a result, the use of FIFO devices and nebulizers may in some cases be discouraged during times when infectious diseases are spreading [James A. McGrath, Andrew O'Sullivan, Gavin Bennett, Ciarrai O'Toole, Mary Joyce, Miriam A. Byrne, and Ronan MacLoughlin. Investigation of the Quantity of Exhaled Aerosols Released into the Environment during Nebulisation. Pharmaceutics. 2019 February; 11(2): 75; Barker et al. COVID-19: community CPAP and NIV should be stopped unless medically necessary to support life. Thorax 2020; 75: 367].

Known measures for removing contaminated room air may include airborne infection isolation room (AIIR), formerly termed: negative pressure rooms. Such rooms are expensive to construct and are not prevalent in all hospitals and long term facilities. Such rooms may also be less efficient in removing contaminated air within the proximity of infected patient's face. The refitting of an existing room to accommodate negative-pressure isolation was assumed to cost $120,000 per room [David W Dowdy, Amelia Maters, Nicole Parrish, Christopher Beyrer, and Susan E. Dorman. Cost-Effectiveness Analysis of the Gen-Probe Amplified Mycobacterium Tuberculosis Direct Test as Used Routinely on Smear-Positive Respiratory Specimens. JOURNAL OF CLINICAL MICROBIOLOGY 2003; 41: 948-953].

Patients with lung and/or heart diseases having a respiratory system that suffers e.g. from insufficiency of oxygenation and/or ventilation may nevertheless require respiratory support.

Insufficient oxygenation means that lung alveoli (i.e. gas exchanging units of the lungs) fail to supply sufficient oxygenated blood to body tissues. Whatever the underlying cause is, typical treatments may include the following types of therapies.

A first therapeutic type may be defined as aimed at increasing the fraction of inhaled oxygen (FiO2), so that e.g. instead of about 21% oxygen content typically in room air, it is possible to increase FiO2 up to about 100% depending on the supportive measures used. Increasing the inhaled oxygen in certain cases may assist in washing out CO2 from the anatomic dead space (ADS) of a patient, e.g. by controlling a relative high inflow of such inhaled oxygen. The ADS of the respiratory system refers to the space in which oxygen (O2) and carbon dioxide (CO2) gasses are not exchanged (or diffused) across the alveolar membrane in the respiratory tract.

A second therapeutic type may be aimed at increasing the gas pressure in the alveoli in order to keep them inflated especially at the end of expiration, thus providing a greater alveoli area for a greater capability of gas exchange. Some respiratory supportive measures are able to keep alveoli expanded by creating positive end expiratory pressure (PEEP).

Example of such first type therapeutic measures may include the nasal cannula, which is a thin tubing that transports oxygen from an oxygen providing system to the patient's nostrils. This measure increases FiO2, however does not provide PEEP. Another example is an oxygen mask that includes a plastic tubing transporting oxygen from an oxygen system to a patient's face mask. The face mask has a strap for securing the mask to patient's face, and in some cases may also include a unidirectional valve, which allows exhaled air to flow outside of the mask while closing during inspiration to allow fresh oxygen supplied by the supportive measure to be inhaled. Face masks, increase FiO2, and however typically do not provide PEEP or substantial PEEP support. In some cases, facemasks, such as non-rebreathing masks, are disposable and thus are typically manufactured in one adult size, and thus do not provide a good seal with an individual patient's face.

A high flow nasal cannula (HFNC) is an additional example of a supportive measure that increases FiO2, while providing humidified and warmed gas to the patient possibly resulting in washing out the ADS from exhaled CO2-rich gas. A HFNC device provides a substantial constant inflow of FiO2, e.g. at a substantial constant flow rates of about 0.6 to 1 liter per second. This high flow of gas creates the wash-out effect of CO2-rich gas from the ADS. Therefore, when CO2 accumulates due to insufficient ventilation, HFNC therapy helps mitigating this adverse effect.

The HFNC supportive measure may also provide some PEEP, e.g. in cases where the patient's mouth is closed. Another example of a therapeutic measure that creates positive end expiratory pressure (PEEP) may be an endotracheal tube (ET), which is a flexible plastic tube that is placed through the mouth into the trachea to help a patient breathe. The ET is then connected to a (mechanical) ventilator, which delivers oxygen to the lungs.

Non-Invasive Ventilation (NIV) and mechanical ventilation (MV) are examples of respiratory supportive measures that are closed systems for increasing patient's FiO2, creating PEEP, and providing various levels of mechanical ventilation to patient. NIV and MV replace patient's respiratory system, and since they follow the breathing patterns of the patient are not suitable for providing wash-out of the ADS, and actually typically increase the ADS.

Insufficient ventilation means that the mechanisms involved in driving expiratory gas from the lungs to the ambient air (outside of the body), and driving fresh air into the lungs, are insufficient. Expiratory air contains relatively high CO2 and low oxygen content, while inspiratory fresh air contains almost no CO2 and about 21% oxygen.

When patient ventilation is insufficient the result is insufficient removal of CO2 from the body, and the level of CO2 in the body increases. To mitigate this, supportive measures including mechanical ventilation (e.g. MV, NIV) may be used to connect a patient to the ventilator either by an endotracheal tube (ET) or by a tight mask. The ET may be secured tightly to the trachea (the main airway of the patient) connecting the patient to the ventilator, and the tight facemask may be installed over the patient's face with straps fixating the mask to the face and head.

Mechanical ventilation by either method may confer inconvenience to the patient. Straps attaching the mask to the patient e.g. in NIV and MV devices, may inflict pressure over the face and head, and the ET technique typically requires sedating the patient, causing a temporarily unconscious state.

SUMMARY

The following embodiments and aspects thereof are described and illustrated in conjunction with systems, tools and methods which are meant to be exemplary and illustrative, not limiting in scope.

In an aspect of the present invention there are provided embodiments of a personal exhaled air removal (PEAR) system for removing/evacuating exhaled air from a vicinity of a patient.

In at least most embodiments, each PEAR system may be arranged to be exclusively allocated to a respective single patient, whose exhaled air it is adapted to evacuate.

The various PEAR embodiments may thus be seen as being aimed at preventing/limiting room air contamination with contagious particles exhaled by patient(s). Furthermore, various PEAR embodiments may be arranged to provide means to prevent/limit room air contamination with contagious particles exhaled by patient while allowing the use of aerosol generating means/therapies such as HFO or nebulized medications.

PEAR systems in various embodiments may be arranged to include: a patient interface including tubes/conduits in a vicinity of a patient's nose and/or mouth that may be arranged to suck/remove/evacuate the patient's exhaled air during expiration.

In certain embodiments, evacuation of a patient's exhaled air may be substantially only during expiration and not during inspiration of the patient.

A PEAR system may in certain cases be synchronized with a patient's breathing cycle by sensors that may be arranged to detect the patient's breathing cycle.

In certain embodiments, evacuation of exhaled air during a breathing cycle j of a patient may be arranged to start substantially at the end of inspiration j of the patient in order to reach peak capacity of air removal as expiration begins.

In some cases, the evacuation of exhaled air during a breathing cycle j of a patient may be arranged to start at a time/trigger depending on previous inspiration(s) to j (e.g. j−1, j−2 etc.). For example, the time/trigger to start the evacuation of exhaled air may be computed as an average of parameters relating to previous inspiration(s) and/or any other suitable measure (e.g. median, moving average etc.)

Reaching maximal removal capacity of exhaled air at a beginning of expiration may be useful in typical breathing patterns where observations show that most of the breath is exported from the body during the first half of expiration.

In a non-binding example, a PEAR system may be suited to remove exhaled air at a flow rate of between about 1 liter per second to a higher flow rate of e.g. about 10 liters per second (or the like) and possibly more.

Activating removal of air substantially only during an exhalation cycle of a patient, may be useful in substantially avoiding interference between at least certain PEAR system embodiments and possible supportive measures that may be applied for aiding such patient(s).

While such supportive measures typically urge gaseous/ medications towards a patient—PEAR system embodiments of the invention typically act to draw air/gaseous away from the patient—and thus if both may be activated simultaneously for substantial durations of time—such interference may result in sub-optimal treatment to the patient.

In a non-binding example, said supportive measures aiding patients may include respiratory support devices (e.g. high-flow oxygen (HFO) devices) and/or drug delivery devices used for administering medications to a patient (e.g. a nebulizer).

Thus, during inspiration, at least certain PEAR system embodiments may be substantially deactivated during administration of oxygen therapy and/or nebulized medications by supportive measures aiding the patient to breathe. On expiration, such PEAR systems may be activated to remove expired air and decrease/limit risk of transmitting disease e.g. to healthcare workers and other inpatients or visitors.

Air removed by certain PEAR system embodiments may undergo a process of decontamination according to suitable standards [Jane D. Siegel, MD; Emily Rhinehart, RN MPH CIC; Marguerite Jackson, PhD; Linda Chiarello, RN MS; the Healthcare Infection Control Practices Advisory Committee. 2007 Guideline for Isolation Precautions: Preventing Transmission of Infectious Agents in Healthcare Settings. Last update July 2019. https://www.cdc.gov/infectioncontrol/guidelines/isolation/index.html].

In certain cases, removed air may be sampled and assessed for pathogen characteristics such as load within removed air (and the like). Such a test could possibly indicate whether and to what level a certain patient may be contagious.

A patient interface may assume several forms in the various PEAR embodiments. For example, such patient interface can be arranged to include a suction member (e.g. in form of a tube) that may be mounted on an open mask overlying the patient's upper lip.

Such suction member may be mounted on a patient interface unit that can be connected to patient's head. Thus, the patient interface in certain embodiments may be in form of an elastic band that the patient can wear across his/her head and forehead. The suction member can then be mounted in such a way that it will hang in front of patient's face (approx. 15 cm).

The suction member may assume a structure that may be arranged to divert exhaled air in distinct directions in order to assist in collecting, suctioning and removing the exhaled air.

For example, the patient interface and/or suction member may have a formation that expands in both upward and downward directions as it extends away from the patient's face, to form a so-called open "duck beak" formation that acts to urge exhaled air from the mouth to be directed downwards while exhaled air from the nose is directed upwards (relative to the mouth).

Possibly, the patient interface and/or suction member may take form of a blanket or apron, overlying a patient's chest and by that acting to aid in removal of exhaled air that is directed downwards from the patient's mouth/nose towards the chest.

In certain embodiments, an integrated type system may be provided where a supportive measure aimed at aiding a patient and an embodiment of a personal exhaled air removal (PEAR) system—may be integrated together.

For example, a high-flow oxygen (HFO) device may be combined with an embodiment of a PEAR system.

In one such application it is possible to diminish the HFO flow to the patient, during expiration for example by 50%—so that instead of e.g. providing about 40 liters per minute (LPM) of oxygen to the patient during expiration it may be possible to provide only about 20 LPM. The remaining e.g. about 20 LPM may be diverted to the PEAR system during expiration for assisting in operation of at least certain PEAR embodiments.

The diverted HFO and/or dedicated air flow provided to a PEAR system—may be directed in some cases to form a so called 'air curtain' flow through and/or towards another set of tubing of the PEAR system, in certain cases embodied as an "apron" member of the PAER system. For example, such 'air curtain' may be arranged to exit a tubing at a certain point where it may be useful in preventing the patient's exhaled air from spreading within a dwelling where the patient is located. The "air curtain" may thus be seen in certain cases as directing exhaled air in a specific direction, where it is easier to collect the exhaled air by suction by the PEAR system.

For example, if the 'air curtain' is directed to flow from a tubing mounted on a patient's forehead towards an "apron" of the PEAR system e.g. generally mounted on a patient's chest, then such air otherwise possibly used in some cases in a HFO device may now be used during exhalation of the patient to collect and prevent the patient's potentially contaminated exhaled air from spreading e.g. within a room where the patient may be hospitalized. Such "air curtain" facilitated by at least certain PEAR systems may thus aid in directing a patient's exhaled towards an "apron" of the system, where such "apron" may be embodied as tubing generally laid on the patient's chest and arranged to suck air from the environment adjacent the patient.

In certain embodiments, a patient interface of a PEAR system may be formed of two rigid (e.g. plastic) bars, which may be padded with soft material (e.g. silicon) to ease and soften the contact with a patient's skin.

The upper bar may be substantially in contact with a forehead of a patient while the lower bar may be arranged to lie substantially over an upper lip of the patient. Said bars may be arranged to form an open mask structure and may be arranged to connect to each other via two hinges one on each side.

Such hinges may aid in setting an angle between the bars and by that optimize the adjustment of such open mask to a patient's face. Such open mask configuration may serve as a skeleton to which suction members may be attached for removing exhaled air from a patient's vicinity and supplying gas to patient.

Said open mask in some cases may be connected to a rear interference member that may be arranged to connect to the open mask on each side of the mask near the hinges. Such rear interference member (e.g., in form of a strap or the like) may be arranged to surround the patient's head and may be adjustable in length.

In certain embodiments, a patient interface of a PEAR system may come in form of a wide elastic band suitable for surrounding a head and forehead of a patient (e.g., like a bandana). Such configuration may be adapted to have a front piece that can hold a suction member in front of the patient's mouth and nose—in the shape of cone In certain cases, an integrated type system combining supportive measures and a PEAR system—may include first and second tube members. The first tube member may be in form of a suction member arranged for removing exhaled air, while the second tube member may be suitable for supplying e.g. oxygen to the patient.

The tube member suitable for removing exhaled air may be connected at its distal end to a negative pressure pump that applies negative pressure to the tube causing suction at a proximal end of the tube close to the patient. Such negative pressure pump may have a capacity of sucking air at a flow rate of between about 1 liter/second to a higher flow rate of e.g. about 10 liter/second (and the like) and possibly more.

The other proximal end of the tube may be connected to a lower part of patient interface overlying e.g. the patient's upper lip or mounted on the bandana.

In certain PEAR system embodiments, a proximal end of a tube-like suction member may be arranged to include substantial large bore holes through which exhaled air may be sucked into the tube.

In the aforementioned integrated type system including first and second tube members, exhaled air suction by one of the tube members may take place substantially only during expiration, while the other tube member used for supplying oxygen and/or medication to a patient may be attached to the patient interface to a region substantially overlying the patient's upper lip. The tube member supplying oxygen and/or medication to a patient may be operative throughout patient's breathing cycle.

In certain cases, a tube like member supplying oxygen and/or medication to a patient may be in form of a nasal cannula (such as in the system of Vapotherm Inc.). Thus, a patient interface of or associated with a PEAR system embodiment, may be suited to accommodate e.g. a Vapotherm tube, or alternatively an independent tube that may be attached for supplying high-flow oxygen (HFO) to a patient.

It is noted that PEAR embodiments may be suited to include or interface with nebulized medication that may be administered to a patient by any suitable means, and not necessarily via a Vapotherm like system (or alike).

In certain embodiments, a sensor provided for detecting expiration and inspiration of a patient, may be arranged to sense a patient's cycle of breathing. Such sensor in certain cases may be arranged to detect the depth/stage of the patient's inspiration in order to project the extent of the following expiration.

For example, if inspiration is prolonged than more air may be expected to be exhaled, and if inspiration is short than less air may be expected to be exhaled. In certain embodiments, upon detection of termination of inspiration a signal may be sent to activate a pump, possibly instantaneously, to remove exhaled air.

Sensing in the context of the present invention may be obtained in various forms and techniques. For example, sensing could be performed by sensing motion of thorax, change of temperature due inspiration (thermocouple) etc.

In certain embodiments, an indicator is provided inside a PEAR system to detect loss of PEAR function or patient interface disconnection. Such indicator in certain cases may be arranged to sample the concentration of patient byproduct (e.g. $CO_2$, water). Such indicator in certain cases may be arranged to Alarm the staff about the loss of PEAR function (or the like).

In an aspect of the present invention, integrated type PEAR system embodiments are provided with enhanced integration between supportive measure and PEAR system functionalities. In certain embodiments, a supportive measure may be auxiliary to a PEAR system that it is arranged to function with, and in other embodiments, the supportive measure may be integral to a PEAR system that it is arranged to function with.

Such integrated type enhanced PEAR embodiments are arranged to combine enhanced breathing supportive functionalities with personal exhaled air removal functionalities described in the embodiments herein above and/or in those PEAR embodiments to be disclosed herein below.

In certain embodiments, such PEAR systems may be arranged to attach to a patient at a mask via which airflows are communicated back and forth between a patient and such PEAR systems.

In at least certain embodiments, enhanced integrated PEAR system embodiments may be arranged to provide a negative (possibly lower than atmospheric) pressure to the mask, in order to increase the driving forces urging airflow from the lungs towards the mask. Assuming air resistance in the human respiratory system is constant, the expiratory flow increases in response to such negative pressure to the mask.

Such greater air driving force provided by at least some PEAR embodiments may assist in providing the desired $CO_2$ wash out from the patient's respiratory system, which in some cases may be seen as a similar functionality to that provided by a high flow nasal cannula (HFNC) device (or the like).

In certain embodiments, such negative pressure may preferably be provided substantially during expiration (and in some cases only during expiration), so that the inspiratory phase of breathing may be substantially less (or substantially not) affected.

Such PEAR system embodiments in most cases may substantially avoid from applying the negative pressure drawing air out of the patient's lungs—when oxygenated gas is directed into the patient's lungs by the supportive measure.

Control of the negative pressure applied by a PEAR system may be facilitated in certain embodiments by provision of a unidirectional valve provided within a mask of the PEAR system that is attached to the patient's face (i.e. such mask being arranged to cover a patient's mouth and/or nose).

Such unidirectional valve may allow air to flow from the outside ambient environment into the PEAR's mask during expiration, so that substantially not all of the negative pressure may be equilibrated with the patient's respiratory system. PEAR systems in certain embodiments may be arranged to function with facemasks that provide a good seal with a patient's face, while in other embodiments may be arranged to function with facemasks that do not necessarily provide a good seal with an individual patient's face, such as disposable masks that are typically manufactured in one size.

In certain embodiments, PEAR systems may be arranged to provide a relative small value of PEEP (e.g. between about 3-5 cm $H_2O$) for assisting in improvement of a patient's oxygenation. Provision of such PEEP may be assisted by the unidirectional valves in the mask, which substantially prevents oxygenated gas directed towards the patient from flowing out of the mask.

In certain embodiments, an incoming airflow provided by a supportive measure of a PEAR system may be controlled and/or chosen to be such that when combined with a patient's inhalation phase may result in a pressure within the PEAR's facemask that is substantially equal to atmospheric pressure. This may be accomplished by controlling/choosing a gas flow provided by a supportive measure into a mask—to be smaller than the inspiration flow created by the patient. In such case, when a patient's inspiration terminates—the pressure within the lung and in the PEAR's mask equilibrate and may both equal substantially atmospheric pressure.

In at least certain PEAR embodiments, once a patient's expiration begins, the PEAR system may be arranged to apply suction and by that reduce the pressure within the mask to below atmospheric pressure, therefore urging flow of gas from the mask possibly to a vacuum tank of the PEAR system.

If a vacuum created by the PEAR system urges formation of a flow that is greater than the flow of air from the lungs to the mask, the unidirectional valve(s) in the mask may open to allow air to enter the mask from the ambient environment in order to equilibrate pressure.

In at least certain PEAR embodiments, the supportive measure (e.g. a HFNC type supportive measure) may be arranged to operate during both inspiration and expiration, however with a contribution to the flow being in the order of about 1 liter/sec which is approximately 15% of the flow from the lungs (7-10 lit/sec). As a result, despite the support provided by the supportive measure, the pressure within the mask may be less likely to increase to above atmospheric pressure during the early phase of expiration.

Towards the end of expiration, at least certain PEAR system embodiments may be arranged to create positive end expiratory pressure (PEEP) within the mask (i.e. pressure in the mask above atmospheric pressure)—by stopping the removal of expired air and allowing the supportive measure to build pressure within the mask, before the next inhalation.

In an aspect of the present invention, control of suction intensity by PEAR system embodiments disclosed herein, may be accomplished in various ways.

In an embodiment, a PEAR system (either of an enhanced or a non-enhanced type) may be arranged to monitor the flow pattern of expiration during the first N breathing cycles of the patient. The outcome of such monitoring may be computation of Q(t-exp), where 'Q' is flow and 't' is time and 'exp' is expiration. This pattern may be translated to a suction flow created by a PEAR system, Q(t-exp-PEAR) that may be arranged to be at a suction level that is greater than Q(t-exp) in order to secure removal of substantially all exhaled air from a patient by the PEAR system, possibly into a vacuum tank of such system(s).

In another embodiment, a PEAR system may be arranged to create a Q(t-exp-PEAR) suction force which may be always substantially greater than Q(t-exp) without necessarily studying Q(t-exp). This may be accomplished by forming a negative pressure which is above the physiologic values of Q(t-exp) of the patient.

In various embodiments, Q(t-exp-PEAR) may be determined by the size of the aperture in the piping flow route that connects the face mask with the vacuum tank, possibly the smallest aperture in such flow route.

In addition to the exemplary aspects and embodiments described above, further aspects and embodiments will become apparent by reference to the figures and by study of the following detailed descriptions.

BRIEF DESCRIPTION OF THE FIGURES

Exemplary embodiments are illustrated in referenced figures. It is intended that the embodiments and figures disclosed herein are to be considered illustrative, rather than restrictive. The invention, however, both as to organization and method of operation, together with objects, features, and advantages thereof, may best be understood by reference to the following detailed description when read with the accompanying figures, in which:

FIGS. 9A to 9C schematically shows a mask of a personal exhaled air removal (PEAR) system in accordance with various embodiments of the present invention.

Figure 1:
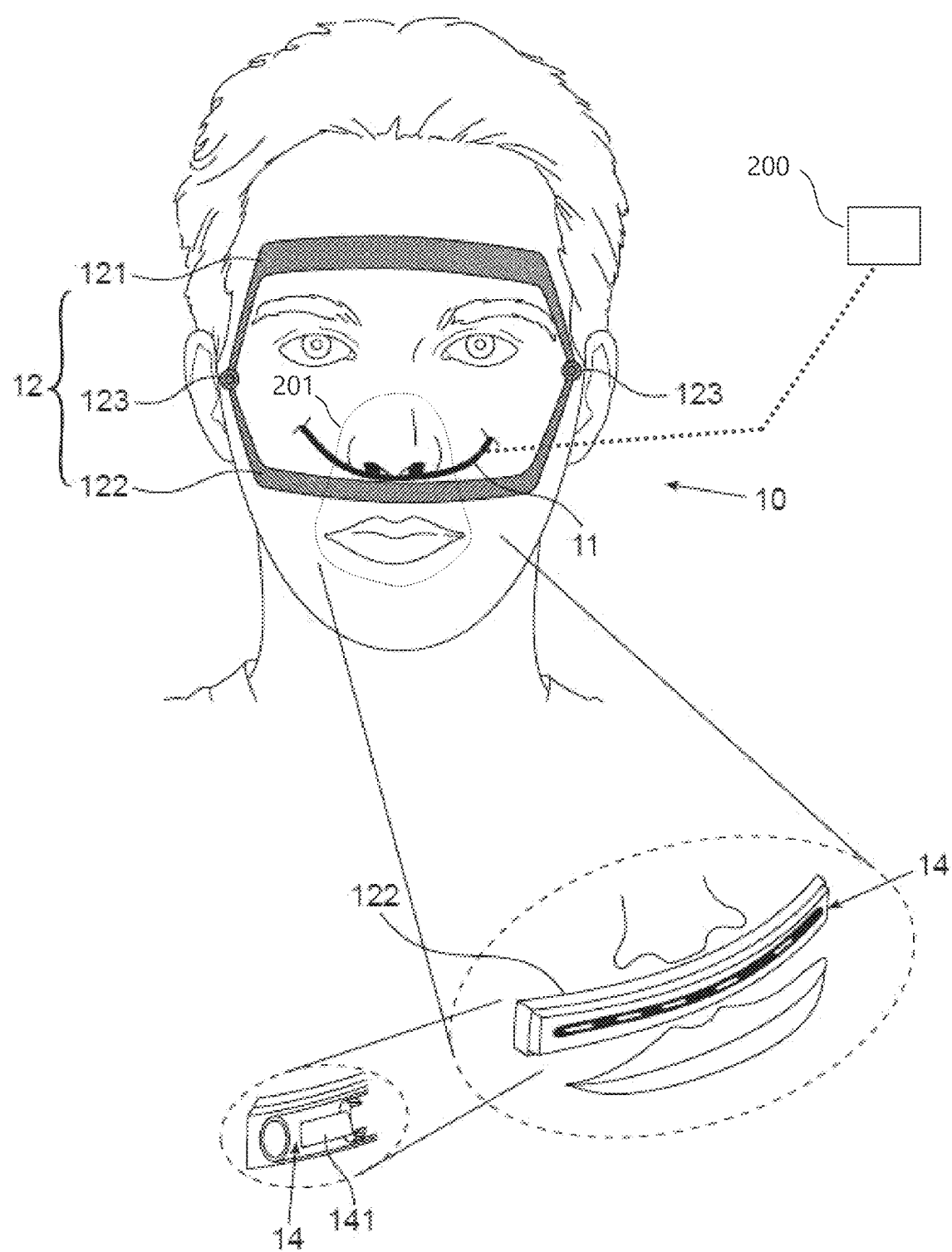
FIG. 1 schematically shows an embodiment of a personal exhaled air removal (PEAR) system of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated within the figures to indicate like elements.

DETAILED DESCRIPTION

Attention is first drawn to FIG. 1 schematically showing one possible embodiment of a personal exhaled air removal (PEAR) system 10 of the present invention.

PEAR systems according to various embodiments of the present invention may be used in conjunction with supportive measure respiratory devices. Here a delivery device 11 of such a supportive measure is illustrated possibly delivering substances from the supportive measure respiratory device.

Certain embodiments of PEAR systems may be arranged to integrally include a delivery device 11 and/or a respiratory device suitable for delivering substances via such delivery device 11 to a patient. However other PEAR system embodiments may be arranged to be used with delivery devices 11 and/or respiratory devices delivering substances via such delivery devices that may be auxiliary and non-integral to the PEAR system.

Such respiratory devices suitable for delivering substances to a patient, in non-binding examples, may include high-flow oxygen (HFO) devices 200, devices suitable for providing medications via nebulizers 201 (or the like). In this example, delivery device 11 is embodied as including an optional nasal cannula 11 for delivering supplemental oxygen and/or medication to the patient.

It is noted that while FIG. 1 illustrates presence of a delivery device 11 hinting to presence of a respiratory device (not shown), PEAR embodiments shown in other figures, although not illustrating a delivery device, can be understood to be possibly suitable for use with such delivery devices and/or respiratory devices.

Powering of suction of a patient's exhaled air by PEAR system embodiments may be achieved by various means. In one example, an embodiment of a PEAR system may be coupled to a suction system typically available in medical facilities, such as in hospitals (or the like). Such suction system may be powered by a central pump station and typically may provide wall outlets to which various medical devices requiring suction may be coupled.

In cases where reliance solely on available suction systems in a medical facility may not be sufficient for effectively evacuating exhaled air of a patient, additional suction utilities may be provided within at least certain PEAR system embodiments.

Figure 7:
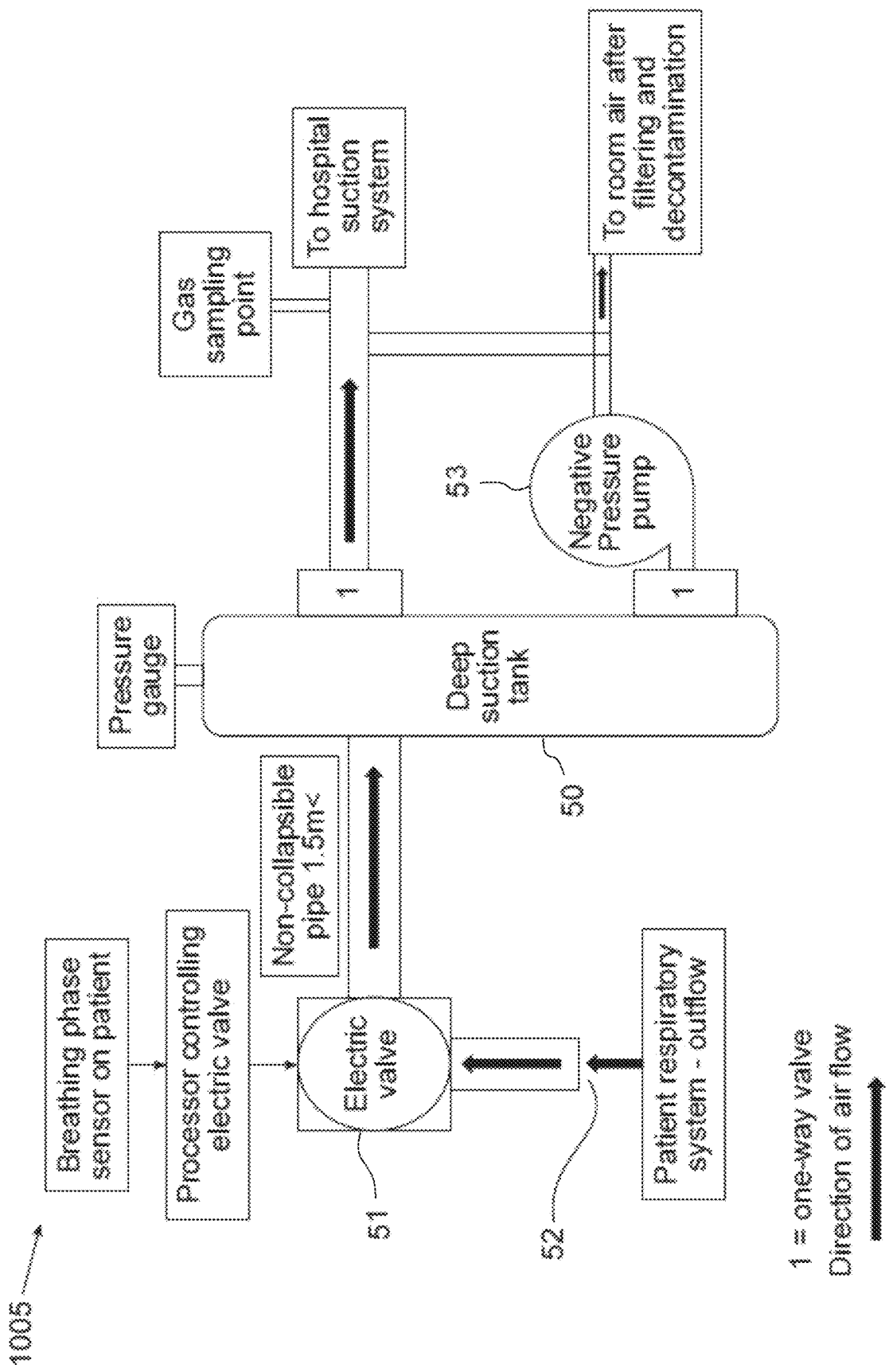
FIG. 7 schematically shows a diagram illustrating components of an embodiment of a PEAR system.

Attention is drawn to FIG. 7 illustrating an embodiment of a PEAR system 1005 that includes a suction tank 50 for assisting in the drawing of air exhaled by a patient.

Negative pressure below pressure present in the ambient environment may be formed within suction tank 50 by a pressure pump 53 in communication with the suction tank via a one-way valve 1. The pressure pump 53 may be arranged to draw air out of the suction tank and by that reduce the pressure within the suction tank.

In a non-binding example, the pressure within suction tank 50 may be formed by pressure pump 53 to be at about 0.2 to about 0.5 bar below the pressure in the ambient environment (e.g. about 0.5 to about 0.8 bar where pressure in the ambient environment is atmospheric pressure, i.e. about 1 bar).

An available suction system in a medical facility where the PEAR system is located, may optionally also be coupled to the suction tank 50 via a one-way valve 1 that permits drawing of air out of the suction tank only.

An electric valve 51, possibly controllable by sensors monitoring a breathing phase of a patient, may be arranged to open a path leading towards the suction tank in order to permit suction of exhaled air via an inlet nozzle 52 of the system that is located adjacent to and/or in communication with the patient's mouth and/or nostrils.

An internal volume of the suction tank 50 may be suited to the amount of exhaled air that the PEAR system may be expected to evacuate in each exhalation phase of the patient. After being opened to evacuate an exhaled breath of a patient, the electric valve 51 may be triggered to close so that a subsequent buildup of negative pressure within the suction tank may initiate. Upon detection of a subsequent exhalation of the patient, the valve may be re-opened to evacuate the next exhalation, and this process may continue as long as the patient is connected to the PEAR system.

Attention is drawn back to FIG. 1. PEAR system 10 in this example includes an optional patient interface 12 formed of two bars 121, 122, that extends laterally along the patient's face. The upper bar 121 is here located above the eyes of the patient, and the lower bar 122 here extends along the patient's upper lip between his/her nose and mouth.

In this example, the bars 121, 122 are interconnected by hinges 123 located on both sides of the patient's head adjacent his/her ears. The hinges may aid in setting an angle between the bars and by that optimize adjustment of patient interface 12 to a patient's face.

The enlarged section at the lower right hand side of the figure reveals an embodiment of a suction member 14 of the PEAR system, here located along the lower bar of the patient interface. The additional enlarged section at the lower left hand side of the figure reveals a possible tube like formation of the suction member 14, including openings 141 through the tube wall, via which exhaled air of the patient may be sucked away and removed from a vicinity of the patient, and preferably removed to a location outside of a room within a dwelling where the patient in located.

Figure 2:
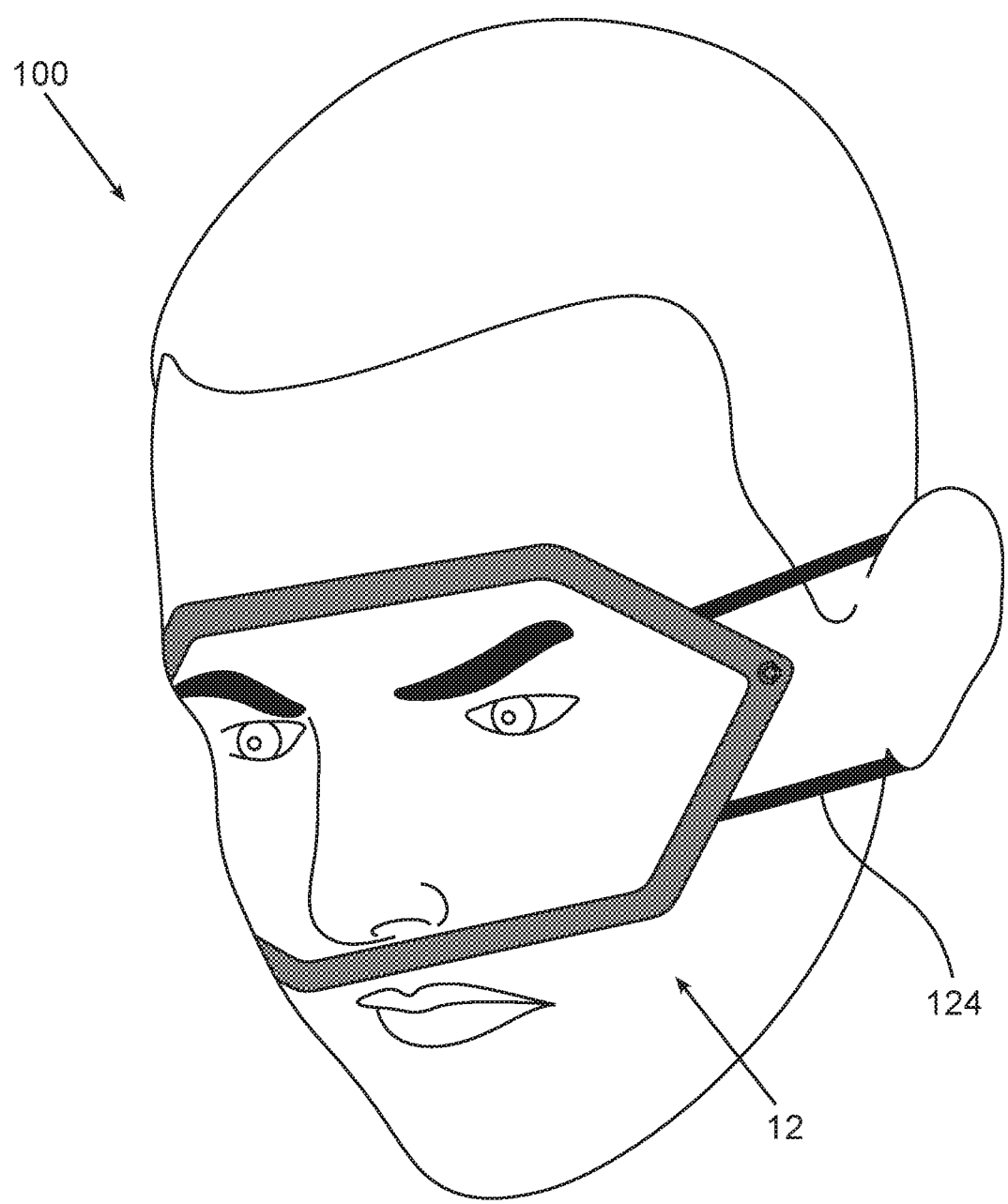
FIG. 2 schematically shows another embodiment of a personal exhaled air removal (PEAR) system of the present invention.

Attention is drawn to FIG. 2 illustrating an embodiment of a PEAR system 100 generally similar to that in FIG. 1, here shown including strap members 124 looping around each one of the ears of the patient to securely attach the PAER's patient interface 12 to the patient's face.

Figure 3A:
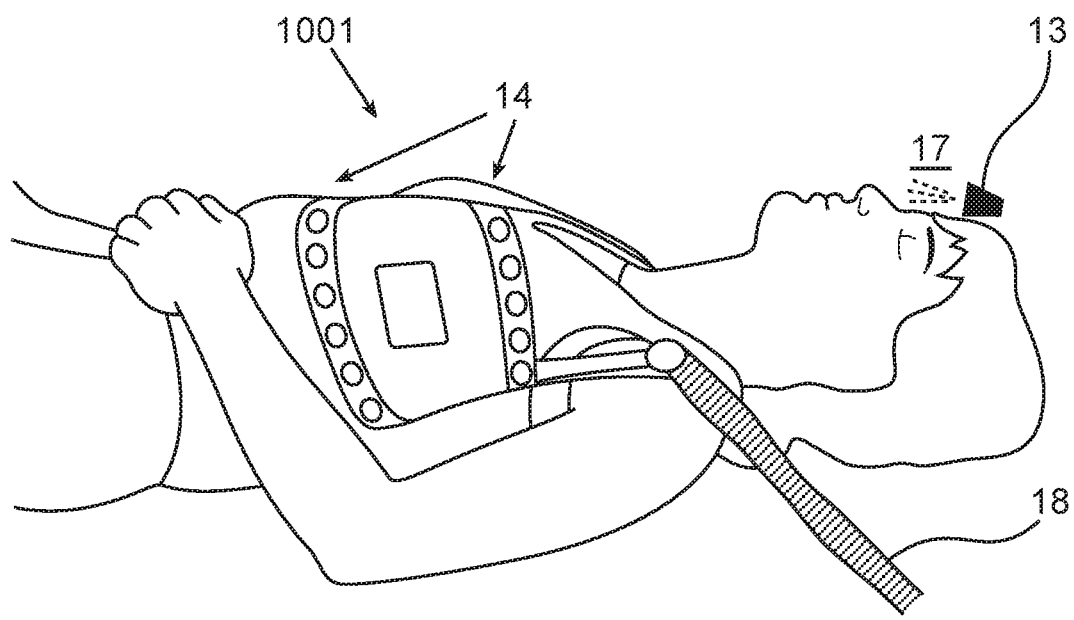
FIGS. 3A and 3B schematically show yet another embodiment of a personal exhaled air removal (PEAR) system of the present invention.
Figure 3B:
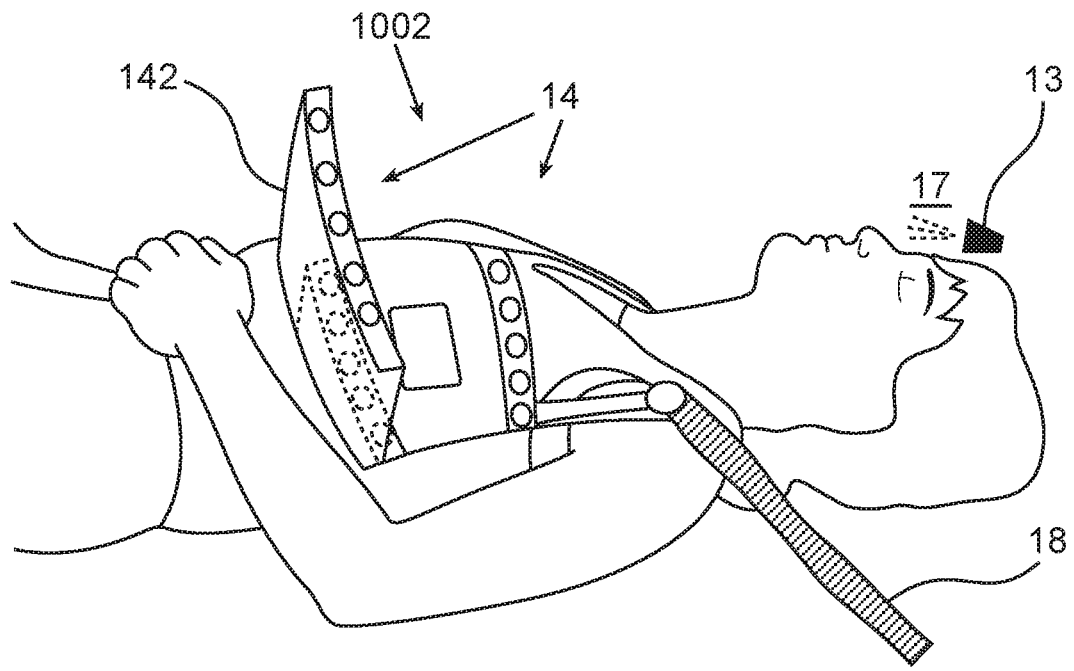

Attention is drawn to FIGS. 3A and 3B illustrating two PEAR system embodiments 1001, 1002 here exemplified located upon chest regions of patients. Both system 1001, 1002 include tube like suction members 14 with openings for sucking exhaled air away from a vicinity of the patient.

While the suction members in system 1001 extend both along the chest of the patient, in system 1002 one of the suction members, here more distal to the patient's head, can be seen being lifted above the patient's chest by a flap like structure 142 of the patient interface.

Both PEAR systems 1001, 1002 illustrate use of an evacuation conduit 18 for evacuating the sucked exhaled air of the patient away from the patient, preferably to outside of a room where the patient is located.

PEAR systems 1001, 1002 are here formed as "apron" like members overlying the patient's chest. In certain cases, such PEAR systems may include a blower 13 arranged to form an 'air curtain' 17 of emitted air flow towards the "apron" like members, where same may be sucked away and removed from a vicinity of the patient—thus assisting in preventing a patient's exhaled air from spreading within a dwelling where the patient is located.

Figure 4A:
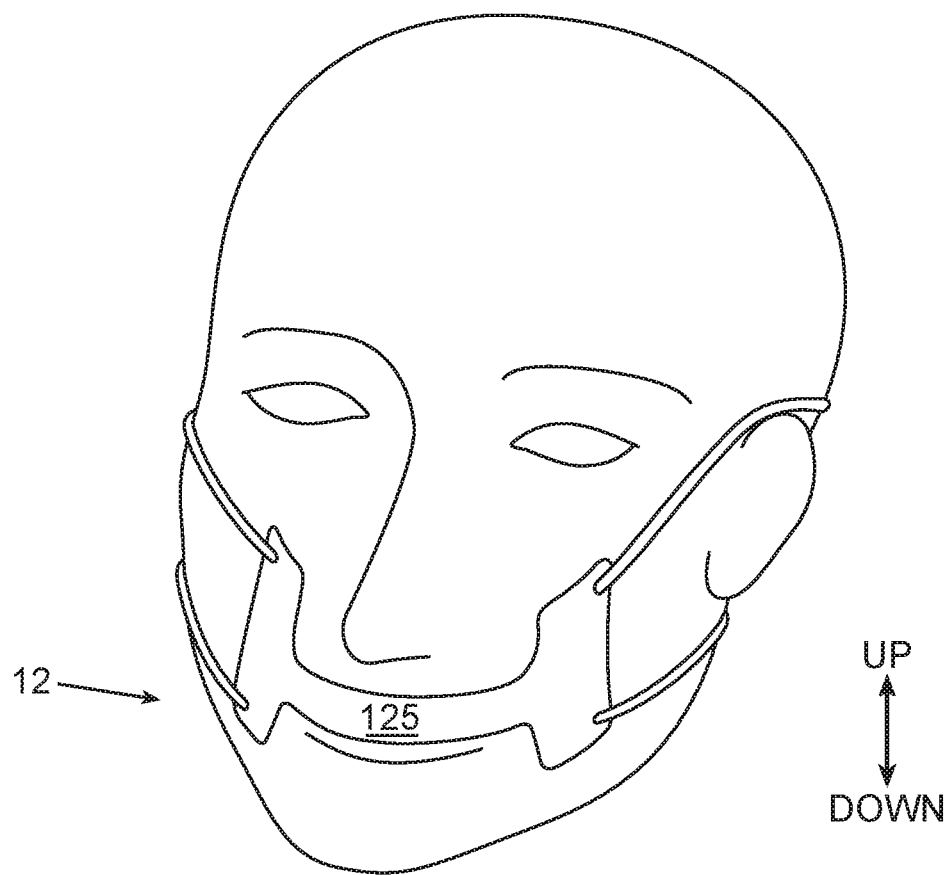
FIGS. 4 and 5 schematically show yet further embodiments of personal exhaled air removal (PEAR) systems of the present invention.
Figure 4B:
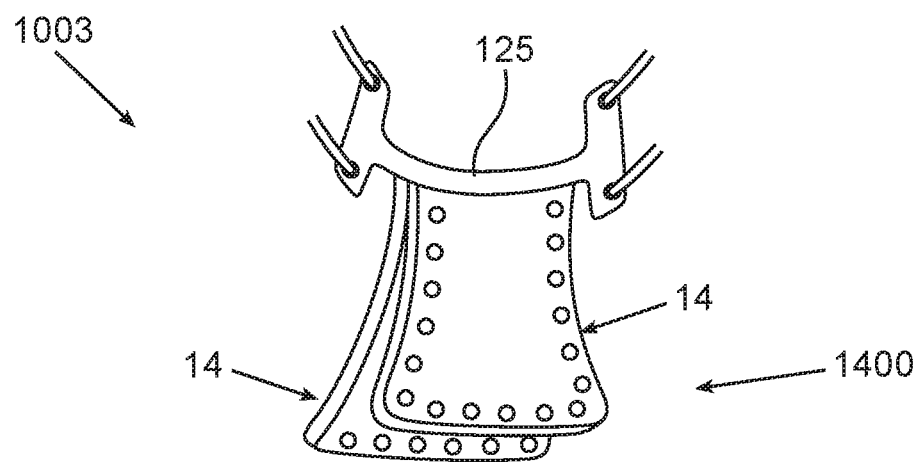

Attention is drawn to FIGS. 4A and 4B illustrating an embodiment of a PEAR system 1003 (see fully in FIG. 4B), which includes a patient interface 12 (see in isolation in FIG. 4A), Patient interface 12 in this example is seen including an H shape with a central section 125 that extends laterally between the nose and mouth of the patient.

PEAR system 1003 in this example includes a so-called open "duck beak" formation 1400 that extends away from central section 125 of the patient interface. Formation 1400 acts to urge exhaled air from the patient's mouth to be directed downwards while exhaled air from the nose is directed upwards (relative to the mouth).

Formation 1400 may include tube like suction members for assisting in suction and removal of exhaled air by the patient.

Figure 5:
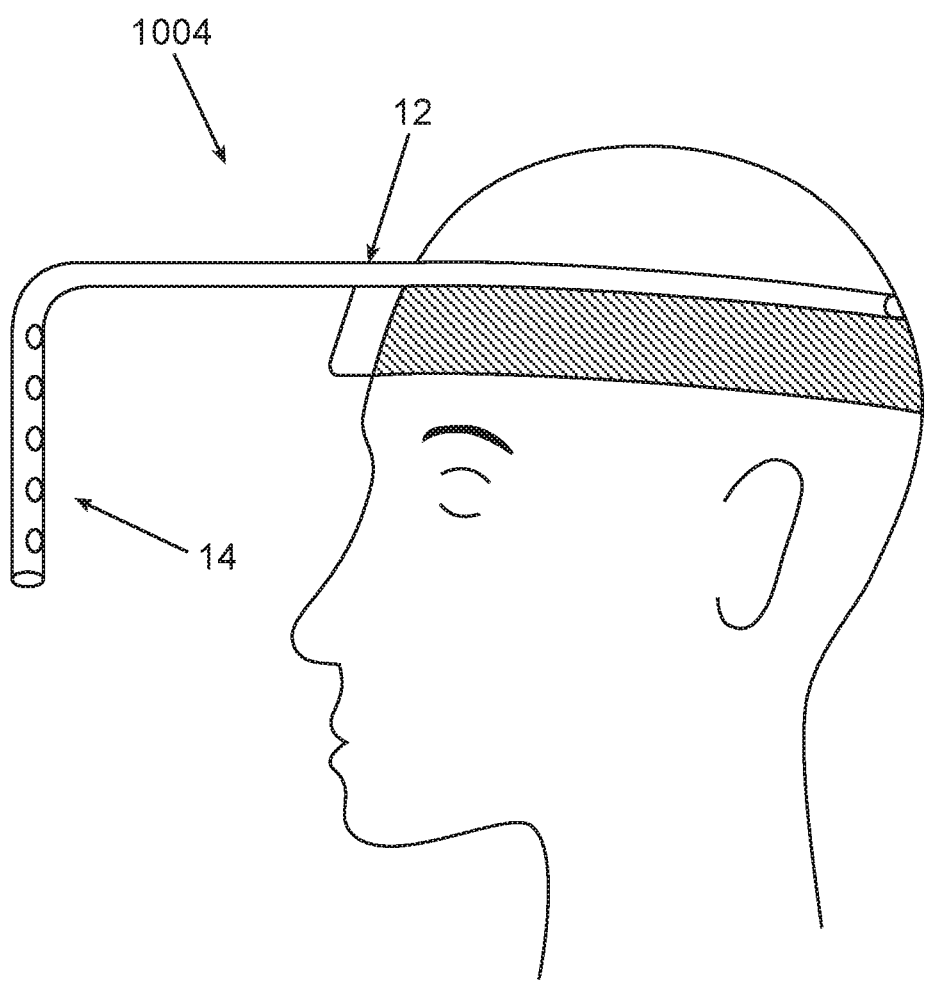

Attention is drawn to FIG. 5 illustrating a further embodiment of a PEAR system 1004. In this example, a patient interface 12 of the PEAR system is seen supporting a suction member 14 in front of the face of the patient to suck exhaled air by the patient.

Figure 6:
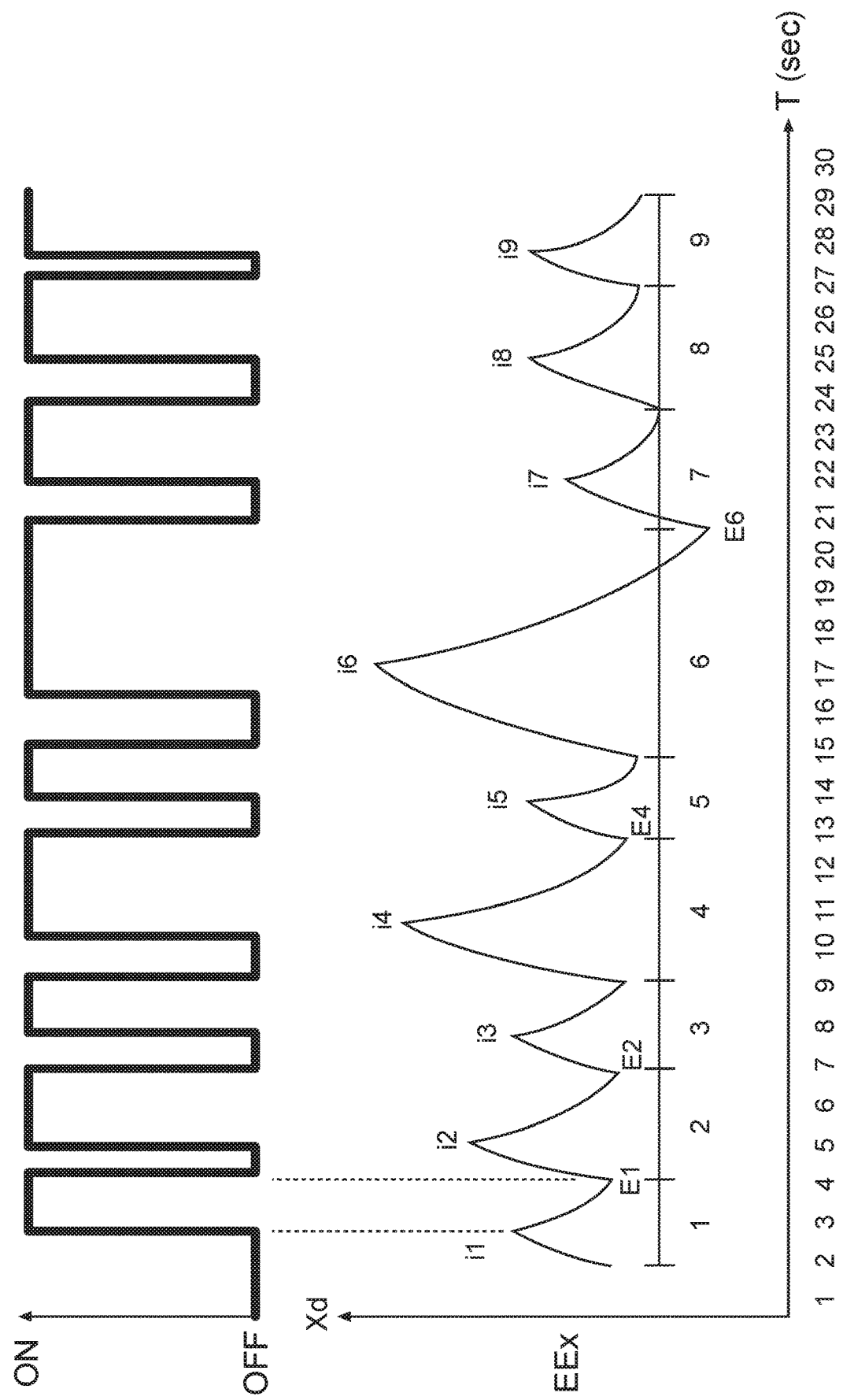
FIG. 6 schematically shows a graph illustrating breathes of a patient.

Attention is drawn to FIG. 6 illustrating at its lower area a graph of recorded patient breaths. Such recording of patient breathes may typically be done in various techniques and using various sensors. In this example, such sensor may be an accelerometer attached to a patient's chest. The y-axis shows displacement of the sensor (units of distance) and the x-axis shows time in second intervals. A patient's inhaled and exhaled volumes may be seen here corresponding to sensor displacement, and transformation of such displacement to volume may be determined according to various functions/correlations.

Breathing cycles in this figure are designated by a horizontal bar and a number indicated below each bar. The first breathing cycle (tagged '1') in this example is at the left hand side of the figure. The cycle starts from a point on the y-axis termed: EEx, where EEx is the point on the trajectory taken by the sensor where the sensor is at the end of "normal" expiration. "Normal" in this context means a resting breathing cycle (e.g. without sighs, coughs, sneezes, etc.).

The inspiratory phase in this example lasts about 1 second (i.e. from about second 2 to 3 along the x-axis) to reach point $I_1$ where it is followed by an expiratory phase terminating at point $E_1$ (in this example at about second 4). Breathing cycle 2 is a bit greater than breathing cycle 11, which means that inspiration is deeper (sensor is more displaced) and expiration is greater, reaching point $E_2$ which also is similar to EEx.

Cycle 3 in this example is generally a normal cycle (generally similar to cycle 1), and cycle 4 shows a greater than normal inspiration, perhaps in a case of a deep sigh or prior to a sneeze, and the expiration of this cycle terminates at point $E_4$ and is also greater than normal. Cycle 5 in this example is again a generally normal breathing cycle, and cycle 6 shows a deep inspiration followed by a large volume expiration. The latter exhaled volume can occur during, for example, a prolonged cough, where intense expiration displaces the sensor to a place which is below EEx. Expiration terminates at a point $E_6$.

Recording the trajectory/indication of the sensor may facilitate in monitoring a patient, e.g. by a physician treating such patient, and by that possibly learning the breathing pattern of the patient. In particular, rate of breathing, variation of depth of breaths, the ratio between duration of inspiration and expiration, number of coughs, sighs, sneezes in a tune interval (and the like), may be learnt. Therefore, in certain embodiments, such breathing data may be recorded and visually presented to a physician treating the patient.

In an aspect of the present invention, the pattern of breathing may be used to provide so-called "landmarks" that may be taken into consideration in activation of suction in at least certain PEAR system embodiments. The upper area of the graph illustrates possible suction actions that may be activated by an embodiment of a PEAR system in response to a sensed breathing pattern of a patient.

For example, by using breathing cycle data (as in FIG. 6 or the like), prediction of magnitude of the expiration of a breath may be taken into account in the activation of an embodiment of a PEAR system. In certain cases, an activation command for suction may be determined by characteristic of the terminal part of the inspiration signal (e.g. by I1, I3, I5), which in certain cases may be characterized by various measures relating to the sensor used for recording breath cycles, such as by such sensor's level of deceleration (or the like).

In yet a further example, percentage of an average inspiratory duration or percentage of an average sensor displacement may be used as input for activating suction of a PEAR system. In the case when a greater than normal expiration may be anticipated, suction may be activated earlier in time or perhaps in a greater than normal magnitude, in order to evacuate a greater volume of patient's exhaled air.

The two dashed lines linking between the lower area of the graph (indicative of a patient's breathing pattern) and the upper area of the graph (indicative of suction operation of an embodiment of a PEAR system)—illustrate an optional possibility where suction by a PEAR system may start generally at an end of an inspiratory phase (here I1) of a given breathing cycle (here cycle 1) and terminate generally at an end of an expiratory phase (here E1) of same given breathing cycle (here accordingly cycle 1).

A normal person (with weight of about 70 kg) evacuates about 0.5 liter of air during exhalation, while the average human respiratory rate is between about 30-60 breaths per minute at birth, decreasing to 12-20 breaths per minute in adults. Taking 12 breaths per minute as the lower limit of breathing rate, renders that such a breathing cycle lasts about 5 seconds and hence the average duration of exhalation is about 2.5 or possibly 3 seconds. As a result, the lower limit of flow rate during exhalation may be about 0.15 liter per seconds (i.e. 0.5 liter divided by 3 seconds=0.1667 liter per second).

In various embodiments, a PEAR system may be suited to remove exhaled air at a substantially higher flow rate to that expected by a typical patient, e.g. at a rate of between about 1 liter per second and a higher flow rate of e.g. about 10 liters per second (or the like) and possibly more. Such lower limit of about 1 liter per second may be substantially greater (i.e. about 5 times greater) than the corresponding lower limit of expected flow rate during exhalation (i.e. about 0.2 liter per second) that PEAR systems of at least certain embodiments of the present invention may suited to safely evacuate.

Figure 8A:
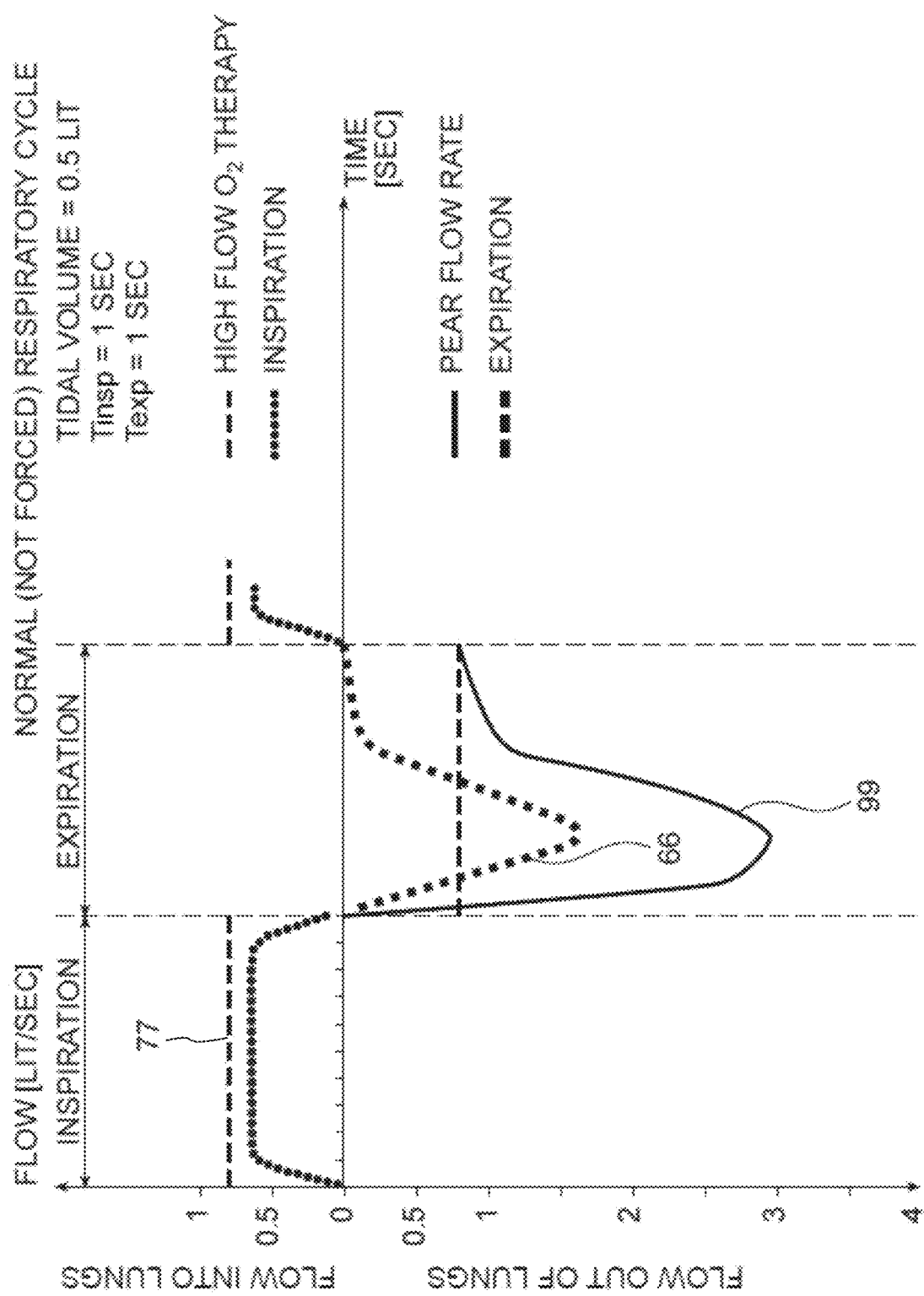
FIGS. 8A and 8B schematically show graphs illustrating operations or various personal exhaled air removal (PEAR) system embodiments during inhalation and exhalations cycles.
Figure 8B:
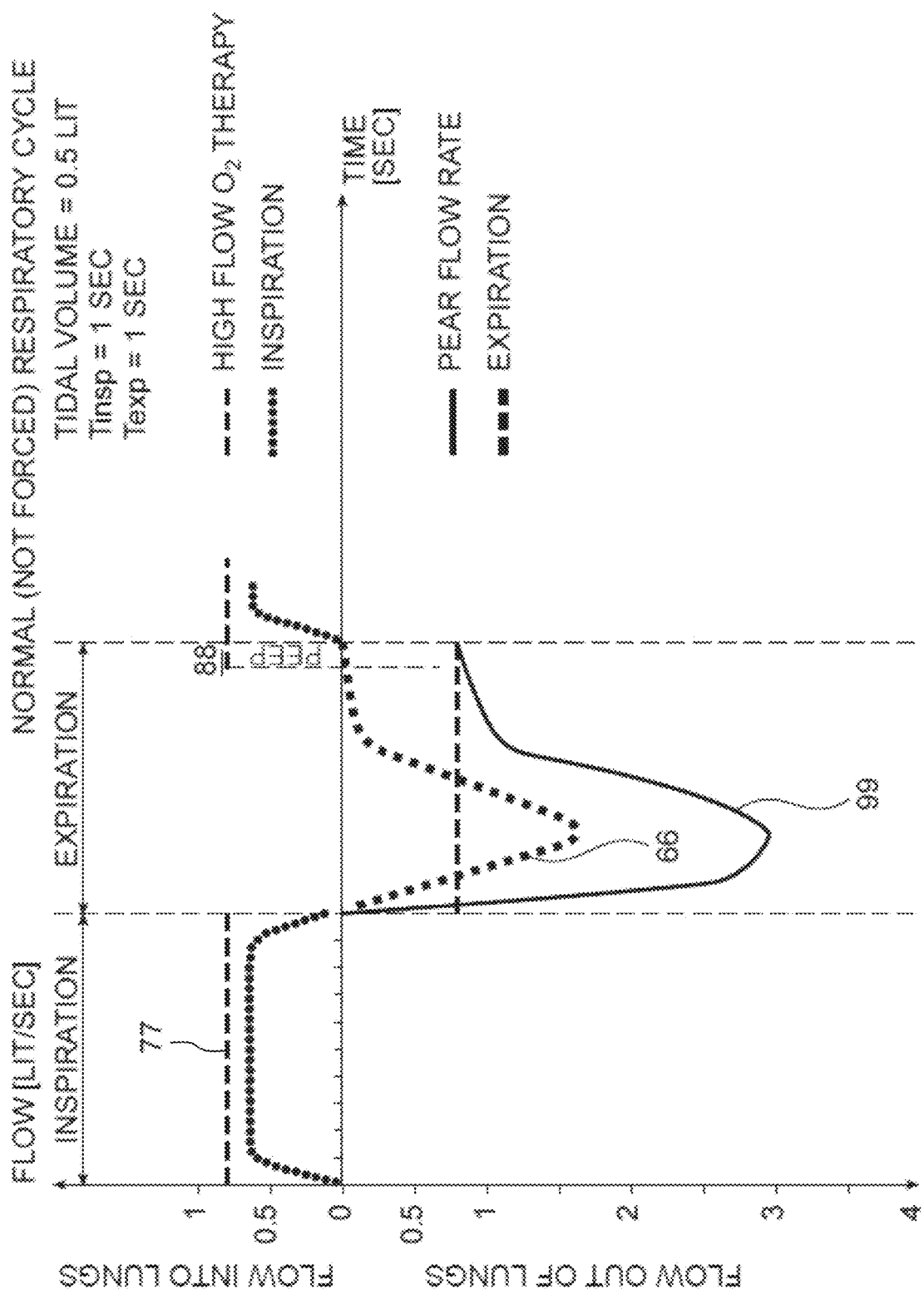

Attention is drawn to FIGS. 8A and 8B schematically illustrating operations or various personal exhaled air removal (PEAR) system embodiments during inhalation and exhalations cycles. These graphs illustrate typical patient breathing cycles coupled with assistance provided by supportive measures, either auxiliary or integral to the PEAR systems, and the exhalation removal sequences provided by such PEAR systems.

In at least certain embodiments, integrated type PEAR system embodiments are provided with enhanced integration between patient supportive measure and PEAR system functionalities. In certain embodiments, a supportive measure may be auxiliary to a PEAR system that it is arranged to function with, and in other embodiments, the supportive measure may be integral to a PEAR system that it is arranged to function with.

The graph provided in FIGS. 8A and 8B illustrate inspiration and exhalation phases of a single breathing cycle, and a sensor provided in (or associated with) such PEAR system embodiments may be suited to detect and monitor these inspiration and exhalation phases.

A supportive measure (such as a high flow nasal cannula (HFNC) type device or the like) may be arranged to continuously provide inhalation support (see indicated by numeral 77) to a patient at a substantially constant flow rate of e.g. between about 0.6 to 1 liter per second. Such inhalation support 77 is noted to preferably continue also during the expiration phase.

Upon detection of start of an expiratory phase of the breathing cycle (or detection during an end of the previous inspiration phase that an expiratory phase is about to start)—the PEAR system may be arranged to start applying a negative suction level 99 that is greater than the flow pattern 66 of expiration by the patient. Preferably, at each instance in time along the time axis, the negative suction level 99 may be greater than the flow pattern 66 of expiration by the patient, with exceptions being e.g. during intentional formation of PEEP as seen in FIG. 8B.

In one example, determining the flow pattern 66 of expiration by a given patient may be Obtained by monitoring the patient's expiratory flow pattern during the first one or more (N) breathing cycles during which the patient is connected to the PEAR system. In other examples, the PEAR system may be arranged to create a suction force that is greater than the maximal expected expiratory flow of a patient, while not necessarily having knowledge of the precise flow pattern that such expiratory phase of the patient may follow.

As seen in FIG. 8B, in certain embodiments provision of a positive end expiratory pressure (PEEP) 88 may be formed by substantially lowering to below the level of the flow pattern 66, or substantially shutting off, the negative suction level 99 applied by the PEAR system towards the end of the expiration phase.

Attention is additionally drawn to FIG. 9A illustrating a mask 44 via which airflows may be communicated back and forth between a patient and at least certain embodiments of PEAR systems. Mask 44 may be coupled in this example by a tube-like communication channel 33 to suction applied by the PEAR system (e.g. to suction applied by suction tank such as 50 seen in FIG. 7) and may include one or more unidirectional valves 22 that may allow air to flow from the outside ambient environment into the PEAR's mask, however not in the other opposing direction.

Such valves 22 thus may permit air to flow from the outside ambient environment into the PEAR's mask during expiration (see FIG. 9B), while sealing egress of air out of the mask during provision of inspiration to the patient via the mask by a supportive measure (see FIG. 9C).

Fp indicates in FIG. 9A the expiration flow of air evacuated by the patient during an exhalation phase of breathing, such as that indicated by numerals 66 in FIGS. 8A and 8B. Fe indicates in FIG. 9A the negative suction flow applied by the PEAR system to evacuate exhaled air by the patient, such as that indicated by numerals 99 in FIGS. 8A and 8B. And Fs indicates air flow entering the mask via the unidirectional valves 22 from the ambient environment.

Fe as already discussed with e.g. respect to FIGS. 8A and 8B, may be arranged to be substantially larger than Fp in order to safely evacuate the exhaled air by the patient. In order to reduce likelihood of formation of negative pressure within the mask, the unidirectional valve(s) 22 may allow air flow to flow into the mask during operation of the PEAR system. In cases where the patient exhales less air, Fs may be urged to be larger than in cases where the patient exhales more air.

A tube like communication channel 55 schematically illustrated in FIG. 9 may be used to channel gaseous from a supportive measure, such as that providing the continuous flow indicated by numeral 77 in FIGS. 8A and 8B, towards the patient.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

Further more, while the present application or technology has been illustrated and described in detail in the drawings and foregoing description, such illustration and description are to be considered illustrative or exemplary and non-restrictive; the technology is thus not limited to the disclosed embodiments.

Variations to the disclosed embodiments can be understood and effected by those skilled in the art and practicing the claimed technology, from a study of the drawings, the technology, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage.

The present technology is also understood to encompass the exact terms, features, numerical values or ranges etc., if in here such terms, features, numerical values or ranges etc. are referred to in connection with terms such as "about, ca., substantially generally, at least" etc. In other words, "about 3" shall also comprise "3" or "substantially perpendicular" shall also comprise "perpendicular". Any reference signs in the claims should not be considered as limiting the scope.

Although the present embodiments have been described to a certain degree of particularity, it should be understood that various alterations and modifications could be made without departing from the scope of the invention as hereinafter claimed.

The invention claimed is:

1. A personal exhaled air removal (PEAR) system for removing/evacuating exhaled air from a vicinity of a patient, the PEAR system comprising:
   at least one vacuum tank for applying suction when suction is activated, and wherein prior to each exhalation phase negative pressure below pressure in an ambient environment is re-created within the at least one vacuum tank;
   a valve that:
   is controllable to open during the exhalation cycle of the patient in order to permit evacuation of exhaled air towards and into the at least one vacuum tank, and
   is controllable to close when the exhalation cycle of the patient ends in order to build up the re-creation of the negative pressure within the at least one vacuum tank;
   wherein the at least one vacuum tank does not collapse inwardly as a vacuum is created in its interior; and
   wherein the PEAR system is configured to evacuate the exhaled air only during an exhalation cycle of the patient, and the PEAR system via a controller is configured to be synchronized with the patient's breathing cycle for activating suction of exhaled air via at least one suction inlet that is adjacent to the patient.

2. The PEAR system of claim 1, wherein evacuation of exhaled air during the breathing cycle of the patient starts substantially at an end of a prior inspiration of the patient in order to substantially reach peak capacity of air removal as expiration begins.

3. The PEAR system of claim 1, wherein the removing of exhaled air is at a flow rate of above about 1 liter per second.

4. The PEAR system of claim 3 and comprising a facemask attachable to the patient and the at least one suction inlet being in fluid communication with an interior of the facemask to evacuate gas from within the facemask during use.

5. A method of using the PEAR system of claim 4, wherein the PEAR system is used in conjunction with a supportive measure providing gas for aiding an inhalation phase of the patient, wherein said supportive measure is an integral part of the PEAR system or auxiliary to the PEAR system, and wherein the supportive measure continuously provides the gas towards the patient.

6. The method of claim 5, wherein the supportive measure is also arranged to communicate with the patient at the facemask, via an inlet formed in the facemask.

7. The method of claim 5, wherein the PEAR system is arranged to direct the gas applied by the supportive measure towards the patient's mouth and/or nose at least when the facemask is attached to the patient's face.

8. The method of claim 5, wherein the supportive measure is a respiratory support device that is any one of the following: a high flow oxygen (HFO) device, a high flow nasal cannula (HFNC) device and a drug delivery device used for administering medications to the patient.

9. The PEAR system of claim 1, wherein the sensor is arranged to detect the patient's breathing cycle in order to control the opening and closing of the valve.

10. The PEAR system of claim 9, wherein the sensor is a temperature sensor.

11. A method for removing/evacuating exhaled air from a vicinity of a patient comprising the steps of:
    providing a personal exhaled air removal (PEAR) system comprising at least one suction inlet,
    placing the at least one suction inlet adjacent to the patient,
    providing a supportive measure for aiding in an inhalation phase of the patient, and
    using the PEAR system and the supportive measure in conjunction while activating suction by the at least one suction inlet of the PEAR system of exhaled air of the patient according to breathing patterns of the patient, wherein
    the PEAR system comprising at least one vacuum tank for applying suction when suction is activated, and wherein prior to each exhalation phase negative pressure below pressure in an ambient environment is re-created within the at least one vacuum tank, and wherein
    the PEAR system comprises a valve that:
    is controllable to open during an exhalation cycle of the patient in order to permit evacuation of exhaled air towards and into the at least one vacuum tank, and is controllable to close when the exhalation cycle of the patient ends in order to build up negative pressure within the at least one vacuum tank, and wherein the at least one vacuum tank does not collapse inwardly as a vacuum is created in its interior.

12. The method of claim 11, wherein the supportive measure aiding the patient lowers its support to the patient during operation of suction by the PEAR system.

13. The method of claim 12, wherein evacuation of exhaled air during the breathing cycle of the patient starts substantially at an end of a prior inspiration of the patient in order to substantially reach peak capacity of air removal as expiration begins.

14. The method of claim 12, wherein the removing of exhaled air via the at least one suction inlet is at a flow rate of above about 1 liter per second.

15. A personal exhaled air removal (PEAR) system for removing/evacuating exhaled air from a vicinity of a patient and comprising at least one suction inlet, the PEAR system being configured to remove the exhaled air during an exhalation cycle of the patient at a rate of above about 1 liter per second, the PEAR system comprising:

at least one vacuum tank for applying suction when suction is activated, such that, prior to each exhalation phase, negative pressure below pressure in an ambient environment is re-created within the at least one vacuum tank, wherein the PEAR system comprises a valve that is controllable to close when the exhalation cycle of the patient ends in order to build up the re-creation of the negative pressure within the at least one vacuum tank, wherein the at least one vacuum tank does not collapse inwardly as a vacuum is created in its interior, and wherein the PEAR system is configured to evacuate exhaled air during a breathing cycle of the patient starts substantially at an end of a prior inspiration of the patient in order to substantially reach peak capacity of air removal as expiration begins.

16. The PEAR system of claim 15, wherein the valve is controllable to open during the exhalation cycle of the patient in order to permit evacuation of exhaled air towards and into the at least one vacuum tank.

17. The PEAR system of claim 15, wherein the removing of the exhaled air occurs substantially only during the exhalation cycle of the patient.

18. The PEAR system of claim 15 and comprising a facemask attachable to the patient and the at least one suction inlet being in fluid communication with an interior of the facemask to evacuate gas from within the facemask during use.

* * * * *